United States Patent [19]
Thornton

[11] Patent Number: 5,125,412
[45] Date of Patent: * Jun. 30, 1992

[54] MUSCULOSKELETAL ACTIVITY MONITOR

[76] Inventor: William E. Thornton, 701 Coward's Creek Rd., Friendswood, Tex. 77546

[*] Notice: The portion of the term of this patent subsequent to May 16, 2006 has been disclaimed.

[21] Appl. No.: 697,341

[22] Filed: May 9, 1991

Related U.S. Application Data

[63] Continuation-in-part of Ser. No. 556,305, Jul. 23, 1990.

[51] Int. Cl.$^5$ .............................................. A61B 5/04
[52] U.S. Cl. .................................. 128/670; 128/710; 128/671; 128/782
[58] Field of Search ............... 128/668, 700, 710, 670, 128/671, 419 PG, 707, 782, 779

[56] References Cited

U.S. PATENT DOCUMENTS

| | | | |
|---|---|---|---|
| 4,827,943 | 5/1989 | Bornn et al. | 128/668 |
| 4,830,021 | 5/1989 | Thornton | 128/707 |
| 4,966,155 | 10/1990 | Jackson | 128/671 |
| 4,974,607 | 12/1990 | Miwa | 128/903 |
| 5,010,893 | 4/1991 | Sholder | 128/419 PG |
| 5,036,856 | 8/1991 | Thornton | 128/710 |

Primary Examiner—Francis Jaworski
Assistant Examiner—George Manuel

[57] ABSTRACT

A musculoskeletal activity monitoring system for use in orthopedic studies in which data from various sensors mounted on a subject are used to monitor the EKG of the subject, as well as, vertical accelerations of the subject and posture of the subject, and in which signals from such sensors are stored and processed over measured time periods to provide desired musculoskeletal activity data.

11 Claims, 6 Drawing Sheets

MUSCULOSKELETAL ACTIVITY MONITOR

This is a Continuation-In-Part of Co-pending application Ser. No. 556,305 filed Jul. 23, 1990. The term of any patent issuing as a result of this application extending beyond the expiration date of U.S. Pat. No. 4,830,021 is hereby disclaimed.

BACKGROUND OF THE INVENTION

Co-pending applications Ser. No. 554,549, filed Jul. 19, 1990; Ser. No. 554,421, filed Jul. 19, 1990; and Ser. No. 555,307, filed Jul. 20, 1990, which issued Feb 19, 1991, as U.S. Pat. No. 4,993,421, all in the name of the present inventor, describe and claim various aspects of a Cardiovascular Monitoring System in which various physical activities of a subject are monitored along with the emotional state of the subject, and certain ambient conditions are also monitored, to determine what effect, if any, the physical activities and emotional state of the subject have normal and abnormal responses in the subject's EKG.

In the monitoring systems described in the co-pending applications referred to above, the monitored signals relating to the physical activity and emotional state of the subject are recorded in conjunction with the recording of the EKG signals. It is suggested in the co-pending applications that the signals relating to the physical activities and emotional state of the subject may be recorded together with the EKG Signals in a single Holter EKG magnetic tape recorder. In such a case, the latter signals are digitized and multiplexed so that they may be recorded on an unused channel in the Holter recorder. As an alternative, and as also suggested in the co-pending applications, the signals relating to the physical activities and emotional state of the subject may be recorded on a separate recorder. The use of a separate recorder has certain advantages since it enables features of the cardiac monitoring systems of the co-pending applications to be used in other fields such as orthopedics and metabolic studies. An objective of the present invention is to provide such a monitoring system which is particularly constructed for use in such other fields.

Specifically, an objective of the present invention is to provide a musculoskeletal activity monitor (MSAM) in which data of the type derived from some of the various sensors described in the co-pending applications, may be used. While some of the physiological signals used in the monitoring systems of the co-pending applications are used in the present system, emphasis is placed on other aspects of the signals and on their processing and display.

Muscle groups and their essential support bones form an inter-dependent musculoskeletal unit. Muscle function provides force and motion and this is transmitted only by attachment to rigid bones. Bones must have strengths (force carrying capacity) at least equal to those of muscle and other applied forces under all conditions or they will fail-break. Normally, this is the case, for over a period of time, muscle and bone will respond to the usual maximum loads placed upon them by hypertrophy or atrophy, such that their capacity always exceeds the usual maximum stress (force) placed on them. This is visibly obvious in the case of, for example, a sedentary clerk as compared with a body builder or sprinter. Less obvious is the difference in their bones which, however, are just as different in their size and strength as are the muscles they must support, for bones hypertrophy as the muscles but much more slowly. For example, bones respond to changes in loads in months while muscles respond in weeks. A major health problem in this country, and in many other countries, is a literal epidemic of broken bones especially of the lower extremities (legs), and particularly the hip which bears large and unique loads. This epidemic affects primarily the older population, and its effects extend beyond the disability of the fracture, because many other systems are adversely effected by the fracture's disability.

While nutrition and hormones play crucial roles in loss of bone strength, it is now recognized that muscle activity, work and exercise, is also crucial to maintenance of adequate bone strength. It is generally recognized that such activity decreases with age and varies with individuals. However, currently there is no way to measure this, and no way rationally to change such behavior.

It is finally being recognized that muscle force, which may be ten times body weight in running, or three times body weight in walking, and not just "weight bearing" (one-half body weight on one leg), is the crucial force.

Unfortunately, there are no practical means available in the prior art to measure quantitatively the activities that affects bones, especially locomotor activity crucial to maintenance of hip strength. Such a monitor which is needed for research and clinical applications will be described in the ensuing specification.

The parameters needed by both researchers and clinicians in the field of bone loss are number of steps, force of steps, time posture (i.e. lie, sit, erect), changes in posture (these changes exert large forces), and it is desirable to know how the locomotor activity effects the cardiovascular system for the cardiovascular system will ultimately limit maximum locomotor rate add activity level.

In addition, the user of such a system needs information in certain format of importance to him. As noted in U.S. Pat. No. 4,830,021, which issued May 16, 1989, to the present inventor, it is very difficult to make Foot Ground Force (FGF) measurements. However, as described in that patent, a relation exists between vertical acceleration signals ($\ddot{Z}$) which allows measurement of step rate and a close approximation of FGF. This data plus an EKG signal allows the needs of researchers and clinicians to be met.

SUMMARY OF THE INVENTION

The invention provides a musculoskeletal activity monitor (MSAM) for use in orthopedic and other studies, in which the data from various sensors used to monitor physical activities and especially locomotion of a subject, are stored and processed in appropriate data reduction units to provide the desired information.

DETAILED DESCRIPTION OF THE ILLUSTRATED EMBODIMENT

Figure 1:
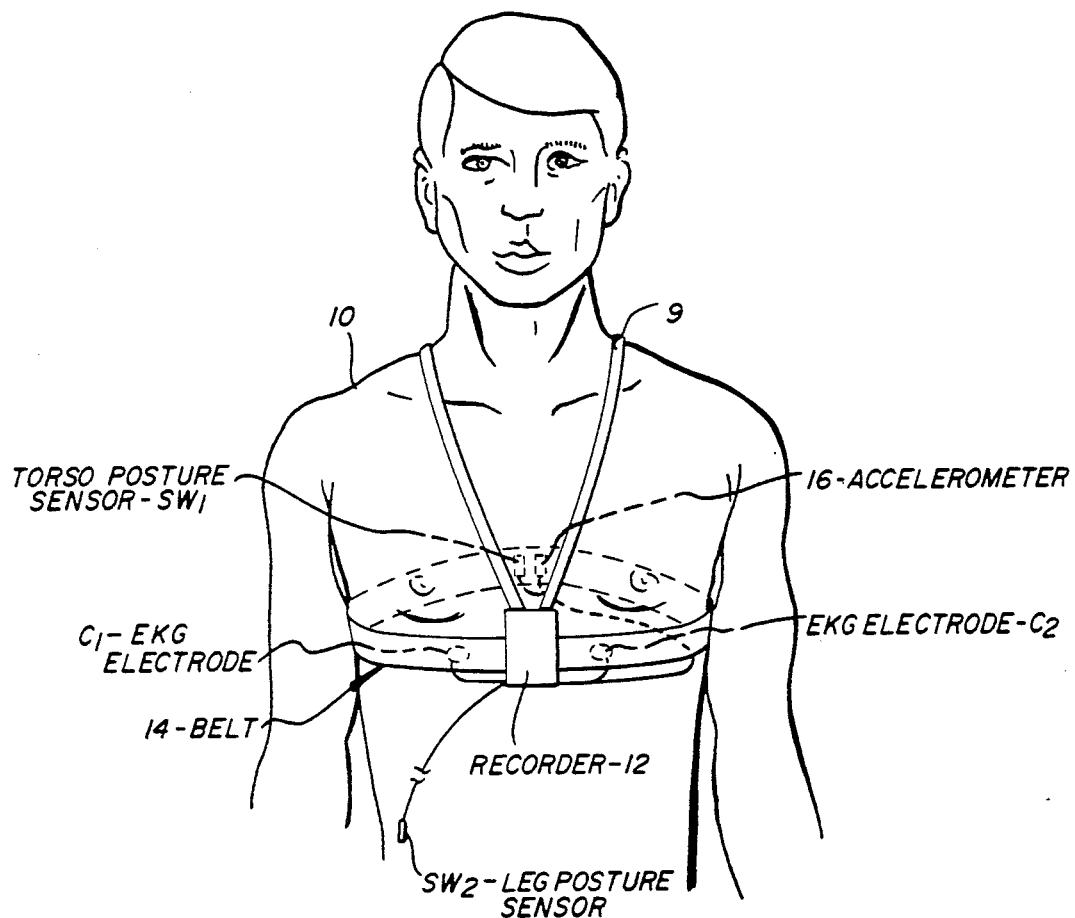
FIG. 1 is a representation of a subject on which various sensors and other instruments are mounted for carrying out musculoskeletal activity monitoring functions.

FIG. 1 is a representation of a subject 10 on which, as mentioned above, various sensors and other instruments are mounted for carrying out the desired musculoskeletal monitoring functions. For example, a small recorder 12 is carried by the subject on a belt 14 or, alternatively in a pocket. Recorder 12 may be a solid state storage and processing system, as will be described. An accelerometer 16 is also mounted on the belt 14, the accelerometer being sensitive in the vertical axis (Z) to accelerations ($\ddot{Z}$). A first position-sensitive switch SW1 is also carried by belt 14, and a second position-sensitive switch SW2 is mounted on the thigh of the subject.

The recorder 12 receives signals from the accelerometer 16, and from switches SW1 and SW2, as well as EKG signals from electrodes C1 and C2 which are also mounted on the subject. If so desired, the accelerometer 16 and trunk position sensor switch SW1 may be mounted on an EKG electrode belt, or in other trunk locations, so long as they are closely mechanically coupled to the center of gravity of the trunk.

Figure 2:
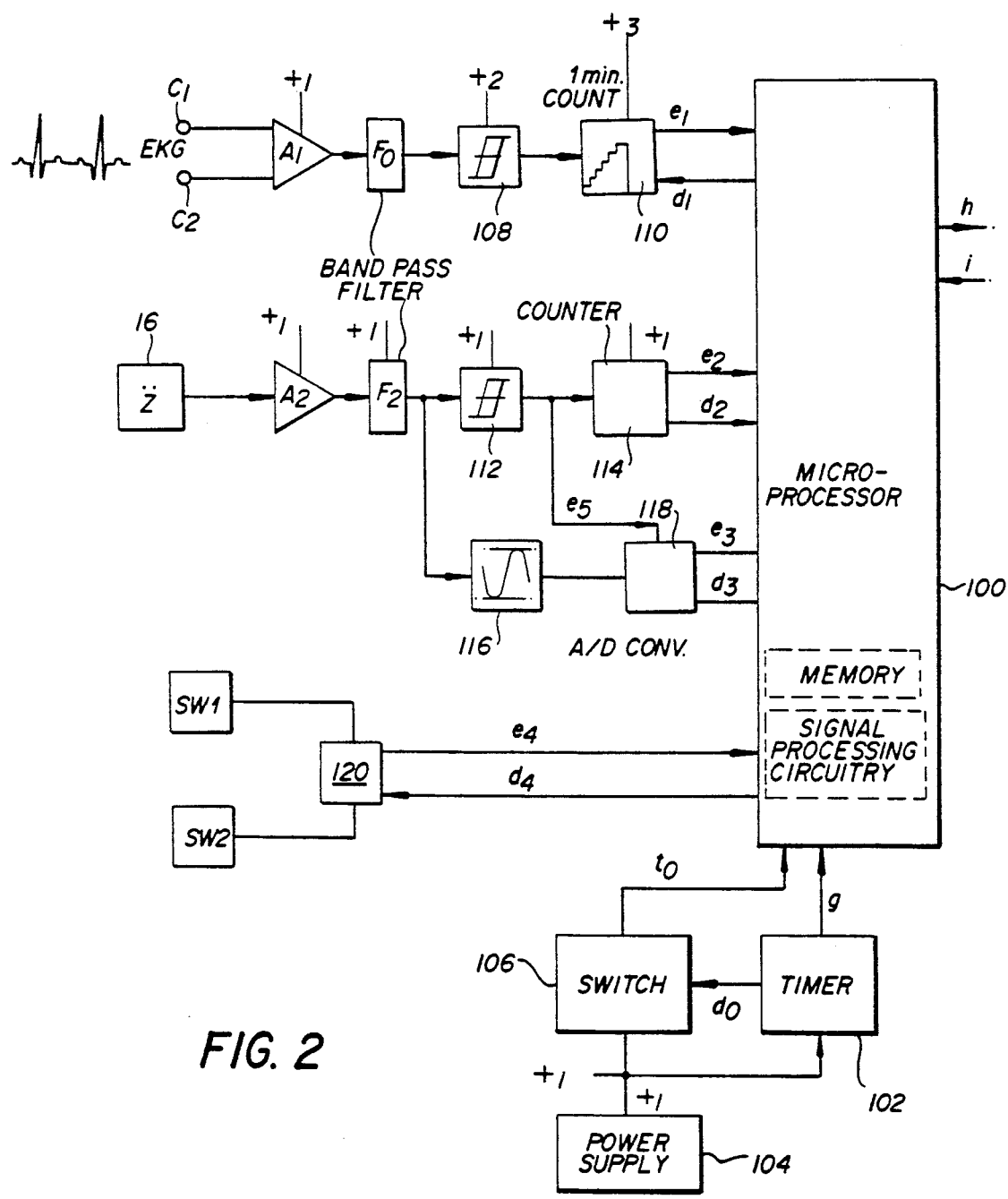
FIG. 2 is a block diagram of various components which are included in a recorder carried by the subject of FIG. 1.

A block diagram of the internal components of recorder 12 is shown in FIG. 2. The recorder of FIG. 2 is a solid state storage and processing unit in which data is stored in the memory of a microprocessor 100, or in a separate memory. The microprocessor may be of any appropriate type, which includes a memory and analog to digital (A to D) signal processing circuitry. The recorder also includes a timer 102 and a power supply 104. A switch 106 is included in the circuit of the power supply 104 and timer 102.

The EKG signals from the electrodes C1 and C2 are introduced through an amplifier A1 and band pass filter F0 (15–19 Hz), so that only the R Wave of the EKG signal is passed to trigger a bi-stable oscillator 108. A small counter 110 (0–256 bits) counts the pulses from oscillator 108. The output of the counter is introduced to the microprocessor over lead $e_1$. An interrogate signal received from the microprocessor over lead $d_1$, resets the counter at the end of each minute. This enables the microprocessor to store the count each minute.

The acceleration signal ($\ddot{Z}$) from accelerometer 16 is introduced to an amplifier A2, and is passed through a bandpass filter F2 (1–10 Hz) to a bi-stable oscillator 112. The output of the bi-stable oscillator 112 is counted in a counter 114, and the count of the counter is likewise stored for each minute in the microprocessor 100 by way of lead e2, with the counter being reset via lead d2. The output of bandpass filter F2 is also passed through peak detector circuit 116. To an analog-digital converter circuitry 118 which includes a digital memory whose output is fed to the microprocessor by way of lead e3 and which is reset each minute by way lead d3. A second control line $e_5$ is connected from the bistable oscillator 112 to the A-D converter 118 such that amplitude-to-digital conversion (typically 0-128 bits) sampling occurs with each step. This data is summed in temporary storage (not separately shown here) once a minute. This summated digital amplitude may then be divided by digital step rate per minute from the counter 114 such that a smaller mean amplitude for each minute may be stored (this process could be delayed with playback and analysis at the cost of portable memory storage space).

A thermistor (not shown) may be mounted on belt 14 adjacent to the subject's skin for sensing skin temperature. An electric circuit similar to the other circuits show in FIG. 2 would then be provided for converting the analog temperature signal produced by the thermistor into a digital signal which would be stored in the microprocessor with the other data each minute, for example. Since increased temperature adds a metabolic load to the body, heart rate (H.R.) is increased for a given level of activity:

$$H.R. = [F_0 t\, f_1(work)] F_2\, (temp).$$

The function F2 is known for previous studies, and with a known temperature. This will be significant in generation of the stress data.

The switches SW1 and SW2 are connected to a combiner two-digit sample count circuit 120, the output of which is applied to microprocessor 100 over lead e4, and which is interrogated each minute by a signal received over lead d4.

The accelerometer 16 carried by the subject measures vertical accelerations (Z) of the subject near his center of gravity. The accelerations ($\ddot{Z}$) may be coverted to vertical forces (Fz) by the system in a manner fully described in U.S. Pat. No. 4,830,021.

The position-sensor switches SW1 and SW2 are attached to the subject, one at his waist and the other at his thigh, as described above. Switches SW1 and SW2 may be commercially available mercury gravity switches, or other appropriate gravity switches may be used. These switches serve to provide signals indicative of the posture of the subject, specifically whether the subject is standing, sitting or lying down. The operation of switches SW1 and SW2 is described in detail in U.S. Pat. No. 4,830,021.

As shown in FIG. 2, accelerometer 16 is connected to amplifier A2 which, in turn, is connected through bandpass filter F2 to bi-stable oscillator 112 which functions as a period detector. The period detector is connected to counter 114 for detecting the frequency of the wave form. The output of counter 114 is introduced to the microprocessor over lead e2, and the counter is interrogated by the microprocessor over lead d2, as described above.

Filter F2 is also connected to a peak-to-peak detector 116 for detecting the amplitude of the wave form. The output of peak-to-peak detector 116 is connected to analog-to-digital converter 118, as is the output of bi-stable oscillator 112. The converter 118 converts the output of the peak-to-peak detector 116 into corresponding digital signals which are applied to the microprocessor over lead e3, and the circuit is reset by appropriate one minute strobe signals from the microprocessor received over lead d3.

Figure 2A:
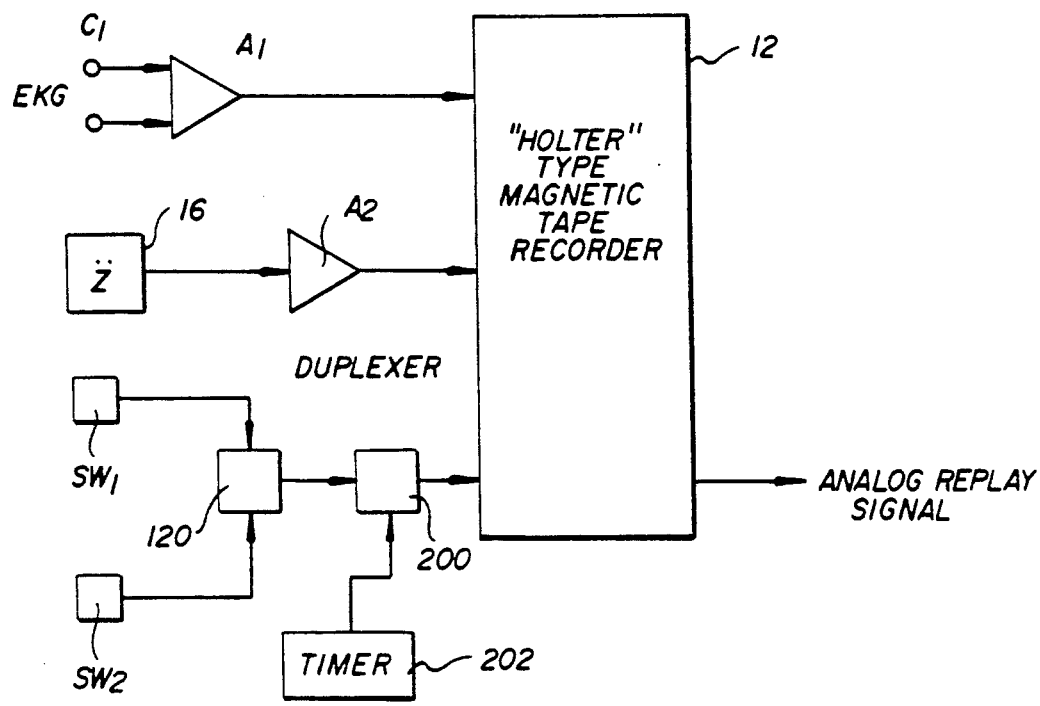
FIG. 2A is a block diagram of a modification to the recorder shown in FIG. 2.

An alternate approach is shown in FIG. 2A in which the recorder 12 is a "Holter" type magnetic recorder, or other type of digital recorder. In the circuit of FIG. 2A the EKG signals from amplifier A1 are applied directly to the recorder, and the vertical acceleration signals from amplifier A2 are likewise applied directly to the recorder. The position signals are applied to the recorder through a duplexer 200 which is controlled by a timer 202. An analog replay signal is derived from the record. However, it is desirable to reduce size and power consumption as much as possible to allow recording for several days, so that the solid state recorder shown in FIG. 2, is preferable.

The EKG channel of the solid state recorder 12 of FIG. 2, uses conventional methodology to amplify and band-pass filter the EKG signals from a bi-polar lead connected to electrodes C1 and C2. As mentioned above, only the R Wave is left to trigger the bi-stable oscillator 108. Counter 110 counts the R Wave triggered events, and its output is introduced to microprocessor 100 over lead e. As explained above the counter is interrogated each minute by a strobe signal received over lead d which resets the counter.

Figure 3A:
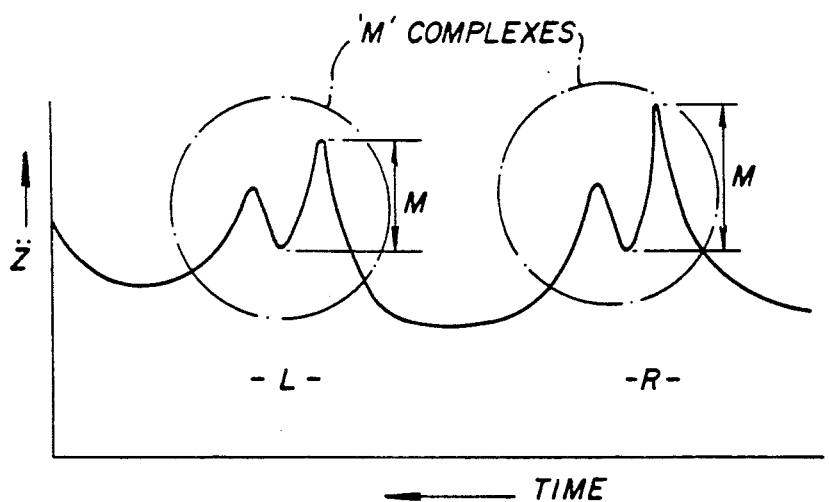
FIGS. 3A and 3B are various vertical acceleration wave forms useful in explaining the operation of the system of the invention.

The acceleration channel processes the acceleration signal ($\ddot{Z}$) in a manner which may be explained with reference to the wave forms of FIGS. 3A and 3B. FIG. 3A is the vertical acceleration wave form during walking where L and R are foot strikes of the left and right feet. During the period where both feet are in ground contact, an "M" shaped complex of fairly high frequency components of, for example, 8-15 Hz, is generated and, as will be shown, is directly related to Foot Ground Force (FGF). The signal also has low frequency components 0.5 Hz to 3 Hz which vary with step rate but which are less well related to FGF during walking.

Figure 3B:
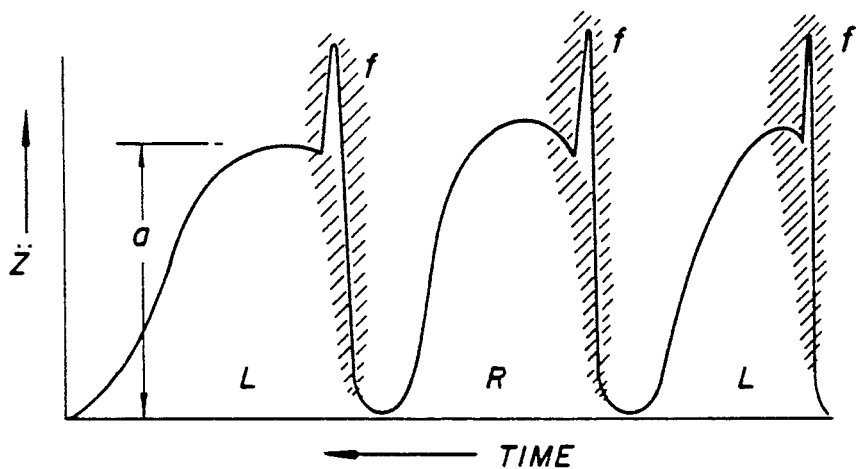

FIG. 3B is the vertical acceleration of wave form during jogging/running, and includes low and high frequency components which are generated on each foot contact L, R, L, etc. The fast component F also lies in the 8-15 Hz region, but is unrelated to Foot Ground Force (FGF), while the remaining low frequency (0.5-3 Hz) signal is directly related to FGF. Step rate, FGF and mode (walk or jog/run), may be measured as follows:

To measure step rate, fast component complexes are filtered in a bandwidth of 8-15 Hz by filter F2, and counted directly by counter 114. In actual practice simpler scheme has been practiced. That is, simply to filter the low frequency component (0.5-3 HZ) of the ($\ddot{Z}$) signal in bandpass filter F2, trigger the trigger circuit 112 by the filtered ($\ddot{Z}$) signal, and then count the complexes of the ($\ddot{Z}$) signal for step rate.

Figure 4:
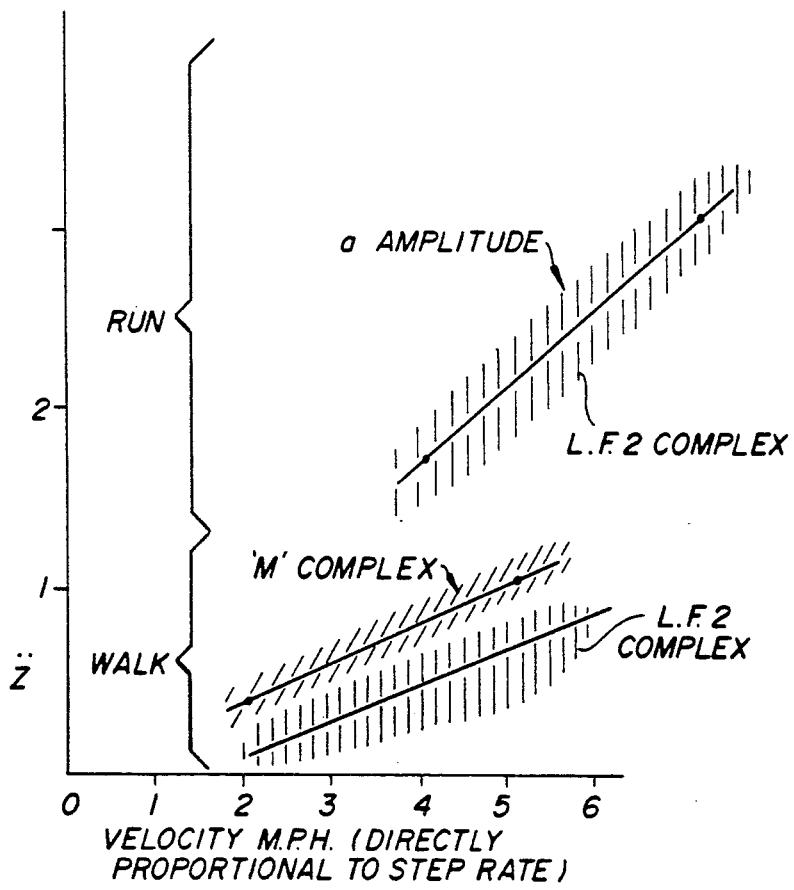
FIGS. 4 and 5 are diagrams relating vertical accelerations and foot ground forces to the speed of the subject.
Figure 5:
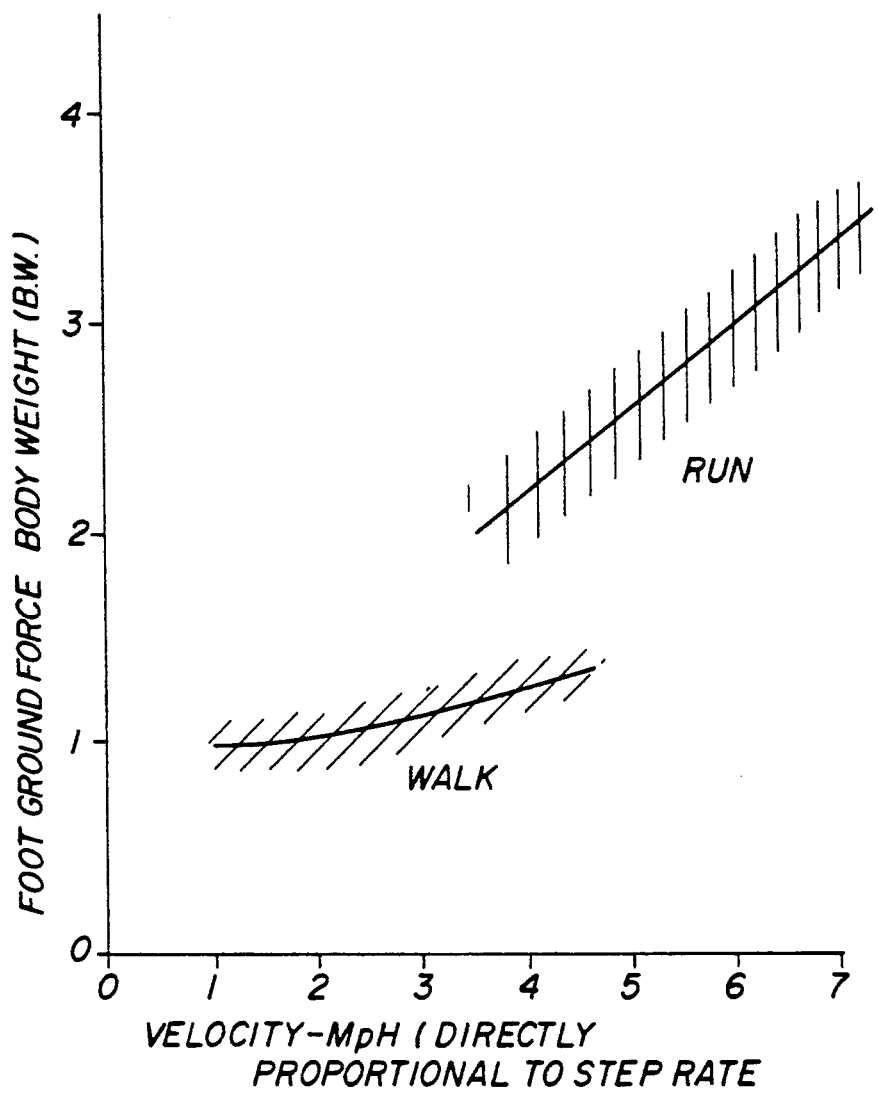

Foot Ground Force (FGF) may be derived from the ($\ddot{Z}$) signal as follows: The high frequency "M" complex of walking, and the low frequency ($\ddot{Z}$) complex of running are directly related to the ($\ddot{Z}$) signal as shown in FIG. 4, and can be measured by filtering (5.-18 Hz) the M complex and the low frequency ($\ddot{Z}$) complex (0.5-3 Hz) signals and peak detecting the signals separately and correcting for the relationship of FGF vs. velocity, as shown in FIGS. 4 and 5.

In practice, there is relatively little change in FGF over the normal range of walking, and it is easier to estimate this value for walking by counting step rate and using a stored reference table during replay. Running FGF's are measured directly from the low frequency ($\ddot{Z}$) complex.

Walking and running low frequency complexes are both stored in the recorder of FIG. 2 in the following manner: After the accelerometer signal ($\ddot{Z}$) from accelerometer 16 is amplified by A2, filtered by F2 (0.5-3 Hz) and amplitude detected by peak detector 116, its amplitude is digitized in the analog-to-digital converter 118 and summed for each minute by the converter. The output from the converter is transferred to storage in the microprocessor 100 via leads e3 on command received over lead d3 which resets the converter 118 to zero.

The same low frequency complex ($\ddot{Z}$) is filtered and used directly to count step rate in the recorder of FIG. 2, in the following manner: The bi-stable amplitude detector circuit 112 detects every foot fall (step), and the steps are summed each minute by the 0-256 counter 114. The count of the counter is transferred to storage in the microprocessor 100 each minute over lead e2, as the counter is interrogated and reset by the interrogate signal received from the microprocessor over lead d2.

The body posture, such as lie, sit, stand is detected by the two-state position switches SW1 and SW2 of FIG. 1, as explained in the U.S. Pat. No. 4,830,021. As mentioned above, the two-state position switches SW1 and SW2 detect the times when the trunk and thigh are within horizontal or vertical limits. A conventional denounce circuit may be included to avoid vibration artifacts. The states of the contacts of the switches SW1 and SW2 are converted into one of three states by a two digit sample/count circuit 120 which introduces signals corresponding to the three posture positions to the microprocessor 100 over lead e4 as the circuit is interrogated by the interrogation signal received over lead d4. Accordingly, the posture state of the subject for each minute is stored in the microprocessor 100.

The power supply 104, timer 102 and switch 106, complete the recorder 12. The data stored each minute is time-tagged digitally by the timer 102 by timing signals introduced to the microprocessor over lead g. To save power, the microprocessor 100 is put in a power-down mode by switch 106 and line to for most of each minute, and is powered only during each brief sample period. This allows a single battery in power supply 104 to power the recorder for a week. Since locomotor habits vary greatly from day to day such long sample periods are necessary.

The next essential and unique feature of the system of the invention is replay analysis and reporting. There are two different requirements, namely investigational and clinical. The first requires as much data as possible, while the second requires only enough data to treat the patient.

Accordingly, different formats are required. First, the general data replay will be described for the solid state digital recorder of FIG. 2, described above. Basic required quantities include: (a) time; (b) step rate; (c) Foot Ground Force (FGF) (d) mode (walk/run); (e) posture; (f) postural transitions and (g) heart rate. Of the above, a, b, e and g are recorded directly.

Figure 6:
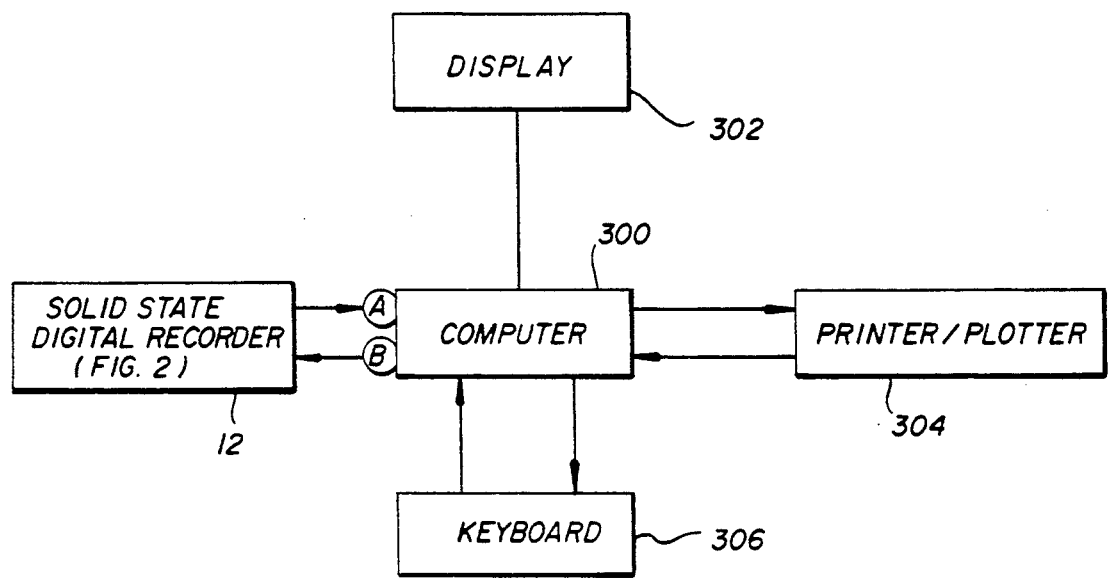
FIG. 6 is a block diagram of appropriate systems for replaying, analyzing and reporting information derived during the operation of the system of the invention.

Replay, analysis and reporting may be carried out by a computer 300 shown in FIG. 6A, and its associated units, such as a display 302, a printer-plotter 304, a keyboard 306. The output from the solid state digital recorder 12 of FIG. 2 is introduced to computer 300 by way of terminal A, as the recorder is interrogated by strobe signals received from terminal B.

The first step is the transmission and storage of the basic parameters listed above, namely, time, step rate, posture, and heart rate into the computer 300 by means of interface circuit K. The remaining quantities are derived as follows:

A. Foot Ground Force (FGF)

If the mode is "run", FGF is derived directly from stored FGF data in accordance with the following equation:

$$FGF = K \cdot (\ddot{Z}) \cdot (L.F.)$$

were K is a proportionality constant near unity.

If the mode is "walk", then FGF will be derived from a fixed look up table stored in the computer as a function of step rate. Such a table is given for example:

| Step Rate | FGF |
|-----------|-----|
| 50–100 | 1. *B.W. |
| 100–110 | 1.1 B.W. |
| 110–120 | 1.2 B.W. |
| 120–130 | 1.3 B.W. |
| 130+ | 1.35 B.W. |

*Body Weight

It should be noted that step rate is linearly related to speed in the walk mode.

If the mode is Mode "jog/run", then referring to FIG. 4, it should be noted that there is a large gap between the ($\ddot{Z}$) L.F. complexes in the "walk" as compared with the run mode. By simple amplitude detection of this stored signal the mode can be detected and used directly, in addition to being used as part of the Foot Ground Force Algorithm.

B. Posture and Heart Rate

Posture and heart rate are obtained directly from the stored signals.

C. Postural Transitions

Postural transitions are counted and identified when going from one state to another.

Digital 302 and Printer/Plotter 304 will display and record the following information.

D. Time Period

The time periods will include total twenty four hours period, any each within 24 hours, and any or all hourly periods within any selected portion of the period. The periods may include:

A. Number of Steps

B. Step rate—mean, maximum, minimum for each mode (walk or jog/run).

C. Foot Ground Force—mean, maximum, minimum for each mode plus the sum of the forces (force/steps x number of steps, for each mode.

D. Posture—Time spent in each posture; a number of transitions from one posture to another (specify).

E. Heart Rate—mean, maximum, minimum.

At this point a program may derive additional relationships not currently available, as described in Appendix A. For example, heart rate vs. various activities, such as, lie, sit, stand, and rates of walking or running B. Graphic records, such as time or bar charts, histograms, etc., may be made of any of the foregoing quantities.

Clinical records may be written summarizing the limited data summaries. For example, total times in various postures and transitions; total locomotor activity including mode, velocities and fores; heart rate for various activities; sleep time. The above will be compared with stored norms for the subject's age, sex, status, etc., and a printed evaluation provided Brevity, data compaction and efficiency are the keys to effectiveness of this report.

The invention provides therefore, a monitor first deriving data relating to the activity of a subject an which is useful in relating such activity to the musculo-skeletal condition of the subject.

It will be appreciated that while a particular embodiment of the invention has ben shown and described, modifications may be made. It is intended in the claims to cover all such embodiments which come within the true spirit and scope of the invention.

APPENDIX A

Heart rate is valuable in many ways in evaluation of capacity for physical activities, for example:

(1) Individual, age related maximum heart rate absolutely limits maximum work rate.

(2) The rate of increase of heart rate with work is an indication of physical condition.

(3) Resting heart rate is also an indication of fitness. N.B. heart rates are temperature corrected.

Figure 7:
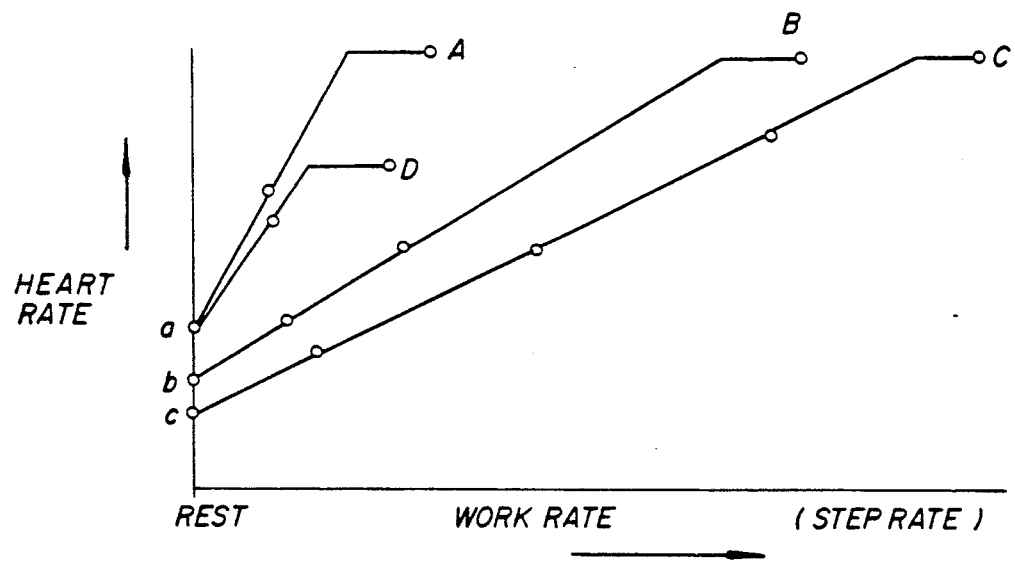
FIG. 7 are curves relating heart rate to the work rate of the subject.

The foregoing is illustrated by the curves of FIG. 7, where A, B and C are records of individuals of the same age and maximum heart rate, but of different levels of fitness, increasing from A to B to C, and indicated by lower resting heart rate (Hr) and slopes (Hr/work). D is an older individual of equal fitness to A.

For first time in ambulatory situations, multiple data can be used to derive additional information which previously required treadmills etc., and frequently was not available except in special laboratories.

It should be noted that theoretical maximum heart rate is derived from empirical formulas of the form of: H.R.max = K-Age (yrs). Usual resting heart rate (URHR) is derived by the computer by taking several minimum heart rates during sitting. Usual sleeping heart rates is derived by the computer by taking means rates during presumed sleep periods (derived from time) when a patient is in a lie posture. It should be noted that this, in turn, can be used to estimate total sleep time by calculating the time when the subject had heart rates (H.R.'s) within sleep limits and was lying and in a presumed sleep.

Estimates of fitness can be derived from the URHR plus the heart rate during known activities, for example, walking/running rates. A plot may be drawn with normal values to indicate relative fitness. Maximum capacity (fitness) is limited by maximum heart rate but the amount of work an individual can do before reaching this point is determined by $URHR_\Delta HR/_\Delta$ work. An estimation of subject "fitness" may be derived as follows. Maximum rate is determined by age A, B, C, D, and URHR as described shown by points a, b, c, on the plot. Work rates are a known linear function of walking (over known limits) and running velocities. In turn velocities are a function of step length and rate which vary linearly and in a known fashion in a given individual. Step length may be estimated from known relations to subject size or by simple measurements. By storing the known relations in the computer plus age and height, work rate may be estimated from step rate and mode (walk or run) which are measured. Since heart rate is known several points may be derived (shown as circles) and the best fit calculated, knowing that heart rate (corrected for temperatures) is a linear function of work or locomotion speed. This can estimate work in conventional terms for the researcher but for the clinician it will be more accurate and convenient to know and prescribe work in terms of step rate is steps min−1. Such estimation of fitness is of great clinical importance in writing activity "prescriptions", patient evaluation, and the like.

I claim:

1. A musculoskeletal monitoring system comprising: acceleration sensor means to be mounted on a subject for measuring vertical accelerations of the subject; EKG sensor means to be mounted on the subject for generating EKG signals relating to the heart of the subject; signal storage and processing means coupled to said sensor means for storing vertical acceleration signals from said acceleration sensor means for successive time periods each of a selected duration, and for storing said EKG signals from said EKG sensor means for said successive time periods, and for processing said acceleration signals to measure the step rate of the subject and to derive the foot ground force of the subject during each of said time periods and to determine whether the subject is in a walking mode or a running mode during each of said time periods, and for producing data relating to the working/running mode, time periods, step rate, Foot Ground Force and heart rate of the subject for each of said successive time periods.

2. The musculoskeletal monitoring system defined in claim 1, and which includes posture sensor means to be mounted on the subject for generating signals related to the posture of the subject; and in which said storage and processing means stores posture signals from said posture sensor means for said successive time periods, and in which said signal storage and processing means produces data related to the posture and postural transitions of the subject.

3. The musculoskeletal monitoring system defined in claim 2, in which said signal storage and processing means includes a microprocessor which in turn includes a memory and signal processing circuitry, and which includes circuitry connected to said posture sensing means to provide signals representative of the posture of the subject during each of a series of predetermined time intervals in response to an interrogate signal from said microprocessor.

4. The musculoskeletal monitoring system defined in claim 1 in which said signal storage and processing means includes a microprocessor including a memory and signal processing circuitry.

5. The musculoskeletal monitoring system defined in claim 4, in which said signal storage and processing means includes circuitry connected to said EKG sensor means and to said microprocessor, said circuitry including a bi-stable oscillator and a band pass filter for passing only the R wave of the EKG signals from said EKG sensor to said bi-stable oscillator to trigger said oscillator, and a counter connected to the output of said oscillator and to said microprocessor to introduce the count of the counter to said microprocessor at the end of each of a series of predetermined time intervals in response to an interrogation signal from said microprocessor.

6. The musculoskeletal monitoring system defined in claim 3, in which said signal storage and processing means includes circuitry connected to said acceleration sensor means and to said microprocessor, said last named circuitry including a bi-stable oscillator and a band pass filter for passing a wave form to said oscillator to cause said oscillator to function as a period detector for said acceleration signals, and a counter connected to the output of said oscillator and to said microprocessor to introduce the count of the counter to said microprocessor at the end of each of said series of predetermined time intervals in response to an interrogate signal from said microprocessor to provide a measurement of the frequency of the acceleration signals.

7. The musculoskeletal monitoring system defined in claim 6, and which includes a peak-to-peak detector connected to the output of said last named bandpass filter, and an analog-digital converter connected between said peak-to-peak detector and said microprocessor to introduce a digital signal to said microprocessor indicative of the amplitude of the acceleration signals during each of said series of predetermined time intervals in response to an interrogate signal from said microprocessor.

8. The musculoskeletal monitoring system defined in claim 7, and which includes a timer connected to said microprocessor to supply timing signals thereto.

9. The musculoskeletal monitoring system defined in claim 8, and which includes a power supply circuit connected to said microprocessor and a switch included in said power supply circuit and controlled by said timer to cause said microprocessor to be energized only during each of a series of sample periods established by the interrogate signals.

10. The musculoskeletal monitoring system defined in claim 4, in which includes computer means connected to said microprocessor and responsive to the data produced thereby for producing data related to foot ground force, heart rate, number of steps, and step rate of the subject during said successive time periods.

11. The musculoskeletal monitoring system defined in claim 10, in which said computer also produces data related to the posture and postural transitions of the subject.

* * * * *